United States Patent [19]

Sheppard et al.

[11] Patent Number: 4,847,078

[45] Date of Patent: Jul. 11, 1989

[54] STORAGE STABLE TOPICAL COMPOSITION HAVING MOISTURE CONTROL AGENT

[75] Inventors: Ray I. Sheppard, N. Miami; Juvenal A. Cuni, Miami, both of Fla.

[73] Assignee: Arseco, Inc., Hyattsville, Md.

[21] Appl. No.: 3,161

[22] Filed: Jan. 14, 1987

[51] Int. Cl.$^4$ .................. A61K 31/79; A61K 31/74
[52] U.S. Cl. ........................................ 424/80; 424/78; 514/777
[58] Field of Search ............... 424/80, 78; 514/777

[56] References Cited

U.S. PATENT DOCUMENTS

| | | | |
|---|---|---|---|
| 2,776,924 | 1/1957 | Martin | 424/80 |
| 2,904,469 | 9/1959 | Nashed | 424/80 |
| 3,041,239 | 6/1962 | Nashed | 424/80 |
| 3,136,696 | 6/1964 | Harrison | 424/73 |
| 3,767,784 | 10/1973 | Gluck | 424/445 |
| 3,859,436 | 1/1975 | Jacobi | 514/23 |
| 3,915,794 | 10/1975 | Zygraich et al. | 424/80 |
| 3,932,615 | 1/1976 | Ito et al. | 424/80 |
| 3,953,591 | 4/1976 | Snyder | 424/80 |
| 4,010,259 | 3/1977 | Johansson | 424/150 |
| 4,045,550 | 8/1977 | Kelly et al. | 424/150 |
| 4,113,851 | 9/1978 | Leveen et al. | 424/150 |
| 4,271,149 | 6/1981 | Winicov et al. | 424/150 |
| 4,301,145 | 11/1981 | Cestari | 424/80 |
| 4,310,513 | 1/1982 | Fauve | 424/80 |
| 4,401,651 | 8/1983 | Knutson | 424/80 |

FOREIGN PATENT DOCUMENTS

| | | |
|---|---|---|
| 15030 | 9/1980 | European Pat. Off. . |
| 80879 | 6/1983 | European Pat. Off. . |
| 180559 | 5/1986 | European Pat. Off. . |
| 1467869 | 1/1969 | Fed. Rep. of Germany ...... 514/777 |
| 1467871 | 1/1969 | Fed. Rep. of Germany ...... 424/361 |
| 1948990 | 5/1970 | Fed. Rep. of Germany . |
| 2036248 | 1/1972 | Fed. Rep. of Germany . |
| 8111720 | 6/1981 | France ............................ 424/361 |
| 55-6613 | 2/1980 | Japan . |
| 1022709 | 6/1983 | U.S.S.R. . |
| 2048070 | 12/1980 | United Kingdom . |
| 2084464 | 4/1982 | United Kingdom . |
| 2092001 | 8/1982 | United Kingdom . |

OTHER PUBLICATIONS

Richard A. Knutson, MD, et al., "Use of Sugar and Povidone-Iodine to Enhance Wound Healing: Five Years' Experience", *Southern Medical Journal.* vol. 74 No. 11, Nov. 1981.
Chemical Abstracts, vol. 99, 1983, p. 354.

*Primary Examiner*—Joseph L. Schofer
*Assistant Examiner*—Peter F. Kulkosky
*Attorney, Agent, or Firm*—Wegner & Bretschneider

[57] ABSTRACT

A storage stable topical composition, especially suitable for pharmaceutical and cosmetic uses, which comprises a topically active ingredient, a sugar, a moisture control agent and a cream base. The carrier cream base comprises one or more from each of the groups of wax compounds, thickening agents and surface active agents dispersed in water.

14 Claims, No Drawings

STORAGE STABLE TOPICAL COMPOSITION HAVING MOISTURE CONTROL AGENT

BACKGROUND OF THE INVENTION

The present invention relates to a sugar-containing composition useful in topical applications having enhanced storage stability and a method for imparting the storage stability to the composition.

One of the primary factors which determines the practical usefulness of a topical cream composition is storage stability. Lengthening of the "shelf life" of a cream prior to the onset of composition separation or crystallization offers obvious advantages such as ease of inventory management, reduction of waste incurred in disposing of creams which are no longer active and removal of the additional burden and uncertainty involved in re-mixing a composition prior to application in cases where this procedure is possible Additionally, when the topical cream is being utilized as a medicament, a further advantage of reduction of inadvertant administration of a composition which can no longer perform its intended function is obtained.

Storage stability of the presently claimed composition is particularly difficult due to the presence of relatively high amounts of sugar in the cream. Sugar compounds are known to dissolve in almost anything having a high moisture content. Obviously, a high moisture content is undesirable for a topical cream composition.

As a result, much effort has been put forth in an attempt to increase the storage stability of topical compositions. See, for example, U.S. Pat. Nos. 4,271,149 issued to Winicov et al. on June 2, 1981, 4,401,651 issued to Knutson on Aug. 30, 1983 and British Pat. No. 2,084,464 issued to Beta Medical Products Ltd. on Apr. 15, 1982.

SUMMARY OF THE INVENTION

Accordingly, it is an object of the present invention to provide a topical cream composition which is storage stable for a long period of time.

It is a further object of the present invention to provide a method for imparting storage stability to topical cream compositions by adding a moisture control agent to the cream.

It is another object of the present invention to provide an improved topical cream composition by adding a sugar and a moisture control aget to the composition.

It is a further object of the present invention to provide a topical cream which can be manufactured in a continuous or discontinuous manner.

It is another object of the present invention to provide a cream base for a topical cream composition comprising wax compounds, thickness and surfactants.

It is a further object of the present invention to provide a topical cream composition which is homogenous throughout.

It is another object of the present invention to provide a topical cream composition of such a consistency to render it capable of being applied directly to the skin or to a dressing material.

Still other objects and features of the present invention will become apparent to those skilled in the art from the following detailed description of the present invention.

DETAILED DESCRIPTION OF THE INVENTION

The present invention contemplates a storage stable topical composition comprising:
 (a) about 5 to about 30% by weight of a cream base wherein said cream base comprises:
  (i) about 5 to about 10% by weight of one or more topically acceptable waxes;
  (ii) about 0.01 to about 5% by weight of one or more topically acceptable thickeners;
  (iii) about 0.5 to about 3% by weight of one or more topically acceptable surfactants; and
  (iv) the balance being substantially water;
 (b) about 0.1 to about 7% by weight of a topically active ingredient;
 (c) about 50 to about 95% by weight of a sugar; and
 (d) about 0.5 to about 2.5% by weight of a moisture control agent.

The present invention further contemplates a storage stable cosmetic composition wherein the sugar level may be reduced to as low as 20% by weight, with the amount by weight of the cream base being adjusted upward as necessary, up to 70% by weight or more. The enhanced storage stability property of the cream compositions is derived from the combination of the ingredients therein which will be discussed in detail below.

The vehicle for the topical composition of the present invention is a cream base made up of one or more compounds chosen from each of the categories of waxes, thickeners and surfactants. Each of the categories and their contribution(s) to the cream base are detailed below.

Wax compounds are useful as emollients and humectants in topical applications. That is, they aid in softening, moisturizing and lubricating the skin. The presence of such emollient/humectant materials promotes the production and application of a cream which will not irritate the skin through abrasion. The wax compounds preferred, according to the present invention, are cetyl alcohol, stearyl alcohol, beeswax, natural or synthetic candelilla, carnauba, jojoba oil, and ceresine.

Thickening agents, as the name implies, serve to add body to the composition by increasing the viscosity of the cream. The presence of such thickeners in a sufficient amount promotes the production of a cream composition of a consistency suitable for topical application. Preferred thickening agents, according to the present invention, are synthetic clays, cellulose ether compounds and polyethylene glycol compounds. Most preferred thickening agents are Laponite XLG (a synthetic clay), Methocel (methyl cellulose), Ethocel (ethyl cellulose), Natrosol (a cellulose ether compound), carboxymethylcellulose and PEG 400 (polyethylene glycol 400).

Surface active agents or surfactants serve a multitude of purposes in topical compositions. The hydrophilic/hydrophobic structural nature of surfactants cause them to orient at solid/liquid or liquid/liquid interfaces. The structure of surfactants also functions to decrease the contractive forces at the juncture of two liquids, the surface tension, thereby promoting the dispersion of one liquid in another. Moreover, these additives promote the dispersion or suspension of solids in a solution. This feature is important in emulsifying the wax compounds, dispersing the thickeners and also providing some assistance in the penetration of the resultant cream into the skin. Preferred surfactants, according to this invention, are polyethylene glycol ether compounds and sorbitan monooleate compounds. Most preferred surface active agents are Tergitol 15-s-9 (a polyethylene glycol ether compound), nonoxynol 9 (nonylphenyl polyethylene glycol ether), and Polysorbate 80 (polyoxyethylene 20 sorbitan mono-oleate).

In addition, some surfactants exhibit anti-microbial properties. The structural nature of these compounds as discussed above permits the surfactants to damage or disrupt the cell membrane of microbes through inactivation of the enzymes which maintain said membranes or by physical disorganization of the membranes. Thus, in certain pharmaceutical and cosmetic uses, the surfactant ingredient(s) may enhance activity.

The topically active ingredient found in the composition is, of course, responsible for the bulk of the activity or useful utility of the present invention. Although the invention is applicable to a cream useful in any topical application, those of a pharmaceutical or cosmetic nature are preferred. Examples of suitable pharmaceutical active ingredients include povidone iodine, bacteriostatic agents, antibiotics, antiinflamatory agents, microbicidal agents and vitamins, while the cosmetic active ingredients include aloe and vitamins.

Suitable bacteriostats according to the claimed invention are acrisorcin, resorcinol, fluorouracil, benzoyl peroxide, dichlorindolene and hexachlorophene, for example Suitable anti-inflammatory agents include, dimethyl sulfoxide, hydrocortizone, betamethasone benzoate and methylsalicylate, for example. Antibiotics usable in the present invention include Bacitracin, Amphotericin B, chloramphenicol and polymyzin B sulfate, for example. Also, vitamins. A and E, for example, are capable of being suspended in a topical cream of the type contemplated by the present invention in both medicinal and cosmetic applications. Finally, suitable microbicides include iodine, gluconate and hydrogen peroxide, for example.

A sugar compound is also present in the topical cream of the present invention. The sugars contemplated by the present invention are mono- and di- saccharide compounds, including their liquid forms and stereoisomers. Preferred sugar compounds are glucose, fructose and sucrose. These compounds provide nutrition to the skin to which the cream is applied, and, in the case of a pharmaceutical use such as antiseptic treatment of an open wound, aid in the healing process Also, some sugars, such as sucrose, exhibit anti-bacterial activity, which enhances the activity of the resultant topical cream. Thus, the cream containing sugar with no other active ingredient will be a useful product.

The moisture control ingredient required by the present claims is, preferably, selected from the group consisting of finely divided silicon dioxide (Cab-O-Sil M-5), anhydrous lanolin and cholesterol. This component absorbs any excess moisture in the topical cream composition thereby maintaining the delicate balance between the ingredients of the cream. Since the equilibrium which exists between the components in the cream is able to be maintained, the tendency for any one of those components to release from the others is reduced.

The storage stable topical cream formulation contemplated by the present invention may be manufactured by art-recognized methodology, with the following set forth as exemplary.

First, the cream based carrier vehicle must be prepared using a standard oil-in-water emulsion technique.

Step 1: In a suitable reaction vessel, 20 to 30 weight % of the total water needed is heated to a temperature in the range of 90°-100° C. Then 0.175-0.4 weight % of a first thickener is added to the heated water, and the mixture is subjected to agitation until a product with the consistency of a paste is obtained. The remainder of the water necessary (to make up the 100 weight % of the cream base given the desired weight percentages of the additives) is added to the paste, and the resultant formulation is agitated until said paste is completely dissolved in the solution. Next, 0.5-3 weight % of a second thickener is added slowly with concomitant mixing until said second thickener is also completely dissolved. A first surfactant is then added, the mixture agitated thoroughly, and the resultant solution is set aside.

Step 2: In a second suitable reaction vessel, the desired waxes, a third thickener and a second surfactant undergo thorough agitation and heating to a temperature in the range of 70°-90° C.

Step 3: Heat the product of step 1 to a temperature in the range of 70°-80° C. Under continual agitation, add the product of step 2 to the heated product of step 1. After the addition is completed, agitation is continued until a cream with a firm consistency and uniform composition is obtained. The firm and uniform cream is then cooled to a temperature in the range of 20°-30° C.

Once the preparation of the carrier cream base is completed, the pharmaceutical cream can be manufactured using standard mixing procedure. The desired amount of the active ingredient is added to the cream prepared above and the mixture is subjected to agitation until the two components are well dispersed. Next the sugar component is added, and the resultant formulation is agitated thoroughly. Finally, the moisture flow control ingredient is added and agitation is applied until a homogenous composition results.

The procedure outlined above is based on production of the topical cream product on a continuous basis. That is, the carrier cream base is utilized immediately after its production in the manufacture of the final product. However, this need not be the case. The simple addition of preservative compound in an amount of about 0.05 to about 0.1% by weight of the cream base to the carrier cream base will allow for discontinuous production of the ultimate topical cream product. That is, the cream base is capable of being formulated at a separate time and/or production facility than the topical cream. Likewise, any combination of the cream base and some of the other three components may be combined separately from the ultimate product. For example, the cream base, sugar and moisture control agent may be preserved and shipped to another site where active ingredient is manufactured. The preservative may be any of those known in the art to preserve such cream bases, preferably povidone iodine or a paraben, for example, methylparaben and butylparaben.

The use of povidine iodine as the active ingredient provides a pharmaceutically effective cream having anti-infective properties. Utilizing the povidone iodine complex rather than iodine itself offers the advantage of increased stability of the iodine in the resultant cream product and enhanced pharmaceutical acceptance without the sacrifice of the anti-infective properties of the elemental halogen compound. Also, povidone iodine is sugar compatible which contributes to the overall stability of the product cream.

A topical anti-infective composition of the present invntion may be applied directly to the injured skin or indirectly to the skin through application to a dressing material or in any other manner known in the art for the juxtaposition of a medicament in cream form with the affected area of the body.

The combination of anti-infective and tissue growth promotion activities of a composition of the present invention renders it useful for treating conditions involving open wounds or burns. The open wounds can be of the type resulting from a skin trauma such as gunshot and knife wounds as well as those induced by other means such as sores or carbuncles.

The unique combination of ingredients found in compositions of the present invention also results in excellent pharmaceutical acceptance. The replacement of elemental iodine with the povidone iodine complex produces drastic improvement in this area. The incidence of skin irritation and staining as well as the onset of allergic reactions often brought on by elemental iodine is reduced very significantly since the PVP-iodine complex is both non-irritating and non-sensitizing. Also, the sugar and other additives are safe for use on human skin, inert to PVP-iodine, i.e., do not react with the complex to release elemental iodine, and compatible with PVP-iodine and each other.

The amount of the active ingredient in the composition, i.e., the dosage required, depends on such factors as the type of injury or dysfunction, the degree of healing which has already been induced, if any, and the skin type of the patient. Those skilled in the art will make an assessment based on these factors and any others which become apparent in the specific case and use the appropriate strength formulation.

When a cosmetic cream is contemplated, the sugar requirement of said cream is reduced. That is, the cream may be formulated with a sugar content as low as 20% by weight of the product cream. This decrease is due to the reduction in the demand for nutrition supplied to the skin. Obviously, a cosmetic designed for routine daily use as a moisturizer or some form of colorant does not require the tissue regenerative capability of, for example, a medicament useful for the treatment of open wounds wherein skin growth is absolutely essential to the healing process. When the amount of sugar is adjusted, the quantity of cream base is oppositely altered to complete the cream composition.

The cosmetic compositions of the present invention may be applied directly to the skin by hand, applicator or in any other manner known in the art for the juxtaposition of a cosmetic in cream form with the desired area of application.

The amount of active ingredient in the cosmetic topical cream, depends on such factors as the intended use of the cosmetic (a corrective moisturizer as opposed to a fortified colorant, for example) and the nature of the skin of the recipient (dry, normal, or oily, for example). Those skilled in the art will make an assessment based on these factors and any others which become apparent in the case of a specific cosmetic and provide the appropriate relative amounts of ingredients.

The topical cream of the present invention exhibits enhanced storage stability properties. That is, the cream does not separate or suffer from the crystallization of the various components suspended in the cream for a long period of time. This results in an increased shelf life and enhanced usefulness of the topical formulation.

It is believed that the proposed moisture-control ingredient imparts much of the marked improvement in storage stability to the composition. This theory is contemplated due to the properties of the sugar ingredient of the cream. Sugars will dissolve in almost anything with a high moisture content. This characteristic is a serious detriment to the formation of a product with the consistency of a cream. However, the moisture control ingredient absorbs the excess moisture and stabilizes the equilibrium between the components of the product cream. Thus, cream compositions containing an effective amount of a moisture control ingredient are capable of maintaining a high sugar concentration dispersed therein for long periods of time.

EXAMPLES

EXAMPLE 1: ANTI-INFECTION CREAM

A. Preparation of the cream base

Step 1: In a suitable reaction vessel, 174.5 ml of water is heated to 95° C. 2.5 gm Methocel is then added., and the mixture is agitated until a paste is formed. 698 ml water cooled to 5° C., is added, and agitation is subsequently applied until the thickener/water paste is completely dissolved. 15 gm Laponite is then added slowly with agitation until the thickener is completely dissolved. 10 gm Tergitol is added, and the resulting mixture is blended and set aside.

Step 2: In a second reaction vessel, 40 gm cetyl alcohol, 30 gm stearyl alcohol, 20 gm polyethylene glycol 400 and 10 gm Polysorbate 80 are heated to 75° C. while agitation is supplied.

Step 3: The mixture of Step 1 above is heated to 75° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 215 gm of the cream base of A above is mixed with 25 gm of povidone iodine until the two components are well dispersed. Next, 750 gm of sucrose is added and the mixture is agitated thoroughly. 10 gm of finely divided silicon dioxide is then added, whereupon the composition is agitated until the final product is homogenous.

EXAMPLE 2

A. Anti-infection Cream

Step 1: In a suitable reaction vessel, 174.2 ml of water is heated to 93° C. 3.0 gm Ethocel is then added, and the mixture is agitated until a paste is formed. 696.8 ml of water having been cooled to 5° C. is added, and agitation is subsequently applied until the thickener/water paste is completely dissolved. 12 gm of Laponite is then added slowly with agitation until the thickener is completely dissolved. 12 gm nonoxynol 9 is added, and the resulting mixture is blended and set aside.

Step 2: In a second reaction vessel, 20 gm ceresine, 40 gm. cetyl alcohol, 10 gm beeswax and 20 gm polyethylene glycol 400 and 15 gm Tergitol are heated to 77° C. while agitation is supplied.

Step 3: The mixture of Step 1 above is heated to 77° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 213 gm of the cream base of A above is mixed with 25 gm by povidone iodine until the two components are well dispersed. Next, 750 gm of glucose is added and the mixture is agitated thoroughly. 12 gm of finely divided silicon dioxide is then added, whereupon the composition is agitated until the final product is homogenous.

EXAMPLE 3: ANTI-INFECTION CREAM

A. Preparation of the cream base

Step 1: In a suitable reaction vessel, 171.6 ml of water is heated to 95° C. 3.8 gm carboxymethyl cellulose is then added, and the mixture is agitated until a paste is formed. 656.6 ml of water having been cooled to 0° C. is added, and agitation is subsequently applied until the thickener/water paste is completely dissolved. 21 gm of Ethocel is then added slowly with agitation until the thickener is completely dissolved. 12 gm Polysorbate 80 is added, and the resulting mixture is blended and set aside.

Step 2: In a second reaction vessel, 30 gm stearyl alcohol, 25 gm jojoba oil, 15 gm ceresine, 20 gm Methocel, and 15 gm Nonoxynol 9 are heated to 75° C. while agitation is supplied.

Step 3: The mixture of Step 1 above is heated to 75° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 205 gm of the cream base of A above is mixed with 25 gm of povidone iodine until the two components are well dispersed. Next, 750 gm of fructose is added and the mixture is agitated thoroughly. 20 gm of finely divided silicon dioxide is then added, whereupon the composition is agitated until the final product is homogenous.

EXAMPLE 4: ANTI-INFECTION CREAM

A. Preparation of the cream base

Step 1: In a suitable reaction vessel, 176.4 ml of water is heated to 100° C. 1.8 gm Natrosol is then added, and the mixture is agitated until a paste is formed. 705.8 ml of water having been cooled to 5° C. is added, and agitation is subsequently applied until the thickener/water paste is completed dissolved. 13 gm of Laponite is then added slowly with agitation until the thickener is completely dissolved. 5.5 gm Tergitol is added, and the resulting mixture is blended and set aside.

Step 2: In a second reaction vessel, 30 gm cetyl alcohol, 30 gm synthetic candelilla, 17.5 gm carboxymethylcellulose, and 20.0 gm Polysorbate 80 are heated to 72° C. while agitation is supplied.

Step 3: The mixture of Step 1 above is heated to 72° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 243 gm. of the cream base of above is mixed with 35 gm. of Vitamin E until the two components are well dispersed. Next, 700 gm. of sucrose is added and the mixture is agitated thoroughly. 22 gm. of anhydrous lanolin is then added, whereupon the composition is agitated until the final product is homogenous.

EXAMPLE 5 ANTI-INFECTION CREAM

A. Preparation of the cream base

Step 1: In a suitable reaction vessel, 172.6 ml of water is heated to 97° C. 2.0 gm Methocel is then added, and the mixture is agitated until a paste is formed. 690.4 ml of water having been cooled to 5° C. is added, and agitation is subsequently applied until the thickener/water paste is completed dissolved. 25 gm of Methocel is then added slowly with agitation until the thickener is completely dissolved. 10 gm Tergitol is added, and the resulting mixture is blended and set aside.

Step 2: In a second reaction vessel, 40 gm beeswax, 30 gm jojoba oil, 20 gm polyethylene glycol 400, and 10 gm Polysorbate 80 are heated to 75° C. while agitation is supplied.

Step 3: The mixture of Step 1 above is heated to 75° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 295 gm of the cream base of A above is mixed with 25 gm of Vitamin E until the two components are well dispersed. Next, 670 gm of sucrose is added and the mixture is agitated thoroughly. 10 gm of finely divided silicon dioxide is then added, whereupon the composition is agitated until the final product is homogenous.

EXAMPLE 6 ANTI-INFECTION CREAM

A. Preparation of the cream base

Step 1: In a suitable reaction vessel, 176 ml of water is heated to 98° C.. 2.5 gm Methocel is then added, and the mixture is agitated until a paste is formed 704 ml of water having been cooled to 0° C. is added, and agitation is subsequently applied until the thickener/water paste is completed dissolved. 7.5 gm of Laponite is then added slowly with agitation until the thickener is completly dissolved. 10 gm Tergitol is added, and the resulting mixture is blended and set aside.

Step 2: In a second reaction vessel, 20 gm cetyl alcohol, 40 gm. natural candelilla, 10 gm stearyl alcohol, and 20 gm Methocel, and 10 gm Tergitol are heated to 75° C. while agitation is supplied Step 3: The mixture of Step 1 above is heated to 75° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 105 gm of the cream base of A above is mixed with 35 gm of povidine iodine until the two components are well dispersed Next, 850 gm of sucrose is added and the mixture is agitated thoroughly. 10 gm of cholesterol is then added, whereupon the composition is agitated until the final product is homogenous

EXAMPLE 7 ANTI-INFECTION CREAM

A. Preparation of the cream base

Step 1: In a suitable reaction vessel, 174.8 ml of water is heated to 90° C.. 2 gm Natrosol is then added, and the mixture is agitated until a paste is formed. 699.2 ml of water having been cooled to 0° C. is added, and agitation is subsequently applied until the thickener/water paste is completed dissolved. 12 gm of Natrosol is then added slowly with agitation until the thickener is completely dissolved. 10 gm Polysorbate 80 is added, and the resulting mixture is blended and set aside.

Step 2: In a second reaction vessel, 30 gm ceresine, 25 gm carnauba, 15 gm cetyl alcohol, and 20 gm carboxymethyl cellulose, and 12 gm Polysorbate 80 are heated to 77° C. while agitation is supplied.

Step 3: The mixture of Step 1 above is heated to 77° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 93 gm of the cream base of A above is mixed with 45 gm of povidine iodine until the two components are well dispersed. Next, 850 gm of glucose is added and the mixture is agitated thoroughly. 12 gm of finely divided silicon dioxide is then added, whereupon the composition is agitated until the final product is homogenous.

EXAMPLE 8 ANTI-INFECTION CREAM

A. Preparation of the cream base

Step 1: In a suitable reaction vessel, 175 ml of water is heated to 92° C.. 2 gm Ethocel is then added, and the mixture is agitated until a paste is formed 702.8 ml of water having been cooled to 5° C. is added, and agitation is subsequently applied until the thickener/water paste is completed dissolved. 12 gm of Ethocel is then added slowly with agitation until the thickener is completely dissolved. 10 gm Polysorbate 80 is added, and the resulting mixture is blended and set aside.

Step 2: In a second reaction vessel, 30 gm stearyl alcohol, 30 gm natural candelilla, 17.5 gm Methocel, and 20 gm Polysorbate 80 are heated to 72° C. while agitation is supplied Step 3: The mixture of Step 1 above is heated to 72° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 283 gm of the cream base of A above is mixed with 55 gm of povidine iodine until the two components are well dispersed. Next, 650 gm of glucose is added and the mixture is agitated thoroughly. 12 gm of finely divided silicon dioxide is then added, whereupon the composition is agitated until the final product is homogenous.

EXAMPLE 9 ANTI-INFECTION CREAM

A. Preparation of the cream base

Step 1: In a suitable reaction vessel, 174.8 ml of water is heated to 91° C.. 2 gm carboxymethyl cellulose is then added, and the mixture is agitated until a paste is formed. 699.2 ml of water having been cooled to 5° C. is added, and agitation is subsequently applied until the thickener/water paste is completed dissolved. 12 gm of Methocel is then added slowly with agitation until the thickener is completely dissolved. 12 gm Tergitol is added, and the resulting mixture is blended and set aside.

Step 2: In a second reaction vessel, 40 gm cetyl alcohol, 30 gm stearyl alcohol, 20 gm polyethylene glycol 400, and 10 gm nonoxynol 9 are heated to 79° C. while agitation is supplied.

Step 3: The mixture of Step 1 above is heated to 79° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 215 gm of the cream base of A above is mixed with 65 gm of povidine iodine until the two components are well dispersed. Next, 700 gm of glucose is added and the mixture is agitated thoroughly. 20 gm of finely divided silicon dioxide is then added, whereupon the composition is agitated until the final product is homogenous.

EXAMPLE 10 COSMETIC CREAM

A. Preparation of the cream base

Step 1: In a suitable reaction vessel, 174.6 ml of water is heated to 95° C.. 2.5 gm Ethocel is then added, and the mixture is agitated until a paste is formed. 698.4 ml of water having been cooled to 5° C. is added, and agitation is subsequently applied until the thickener/water paste is completed dissolved. 12 gm of Methocel is then added slowly with agitation until the thickener is completely dissolved. 7.5 gm Tergitol is added, and the resulting mixture is blended and set aside.

Step 2: In a second reaction vessel, 20 gm ceresine, 40 gm stearyl alcohol, 10 gm beeswax, 20 gm Laponite, and 15 gm Tergitol are heated to 75° C. while agitation is supplied.

Step 3: The mixture of Step 1 above is heated to 75° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 600 gm of the cream base of A above is mixed with 25 gm of aloe until the two components are well dispersed. Next, 350 gm of sucrose is added and the mixture is agitated thoroughly. 25 gm of finely divided silicon dioxide is then added, whereupon the composition is agitated until the final product is homogenous.

EXAMPLE 11 COSMETIC CREAM

A. Preparation of the cream base

Step 1: In a suitable reaction vessel, 172.9 ml of water to 96° C.. 3 gm Laponite is then added, and the mixture is agitateduntil a paste is formed. 691.6 ml of water having been cooled to 0° C. is added, and agitation is subsequently applied until the thickener/water paste is completed dissolved. 20 gm of Ethocel is then added slowly with agitation until the thickener is completely dissolved. 7.5 gm Polysorbate 80 is added, and the resulting mixture is blended and set aside.

Step 2: In a second reaction vessel, 30 gm cetyl alcohol, 25 gm carnauba, 15 gm beeswax, 20 gm Natrosol, and 15 gm Tergitol are heated to 75° C. while agitation is supplied.

Step 3: The mixture of Step 1 above is heated to 75° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 545 gm of the cream base of A above is mixed with 35 gm of aloe until the two components are well dispersed. Next, 400 gm of sucrose is added and the mixture is agitated thoroughly. 20 gm anhydrous lanolin is then added, whereupon the composition is agitated until the final product is homogenous.

EXAMPLE 12 COSMETIC CREAM

A. Preparation of the cream base

Step 1: In a suitable reaction vessel, 173.8 ml of water is heated to 100° C.. 3.5 gm Methocel is then added, and the mixture is agitated until a paste is formed. 695.2 ml of water having been cooled to 5° C. is added, and agitation is subsequently applied until the thickener/water paste is completed dissolved. 20 gm of Ethocel is then added slowly with agitation until the thickener is completely dissolved. 10 gm Tergitol is added, and the resulting mixture is blended and set aside.

Step 2: In a second reaction vessel, 30 gm stearyl alcohol, 30 gm cetyl alcohol, 17.5 gm carboxymethyl cellulose, and 20 gm Polysorbate 80 are heated to 75° C. while agitation is supplied.

Step 3: The mixture of Step 1 above is heated to 75° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 545 gm of the cream base of A above is mixed with 45 gm of aloe until the two components are well dispersed. Next, 400 gm of glucose is added and the mixture is agitated thoroughly. 10 gm of finely divided silicon dioxide is then added, whereupon the composition is agitated until the final product is homogenous.

EXAMPLE 13 COSMETIC CREAM

A. Preparation of the cream base

Step 1: In a suitable reaction vessel, 174.3 ml of water is heated to 95° C.. 3.5 gm Ethocel is then added, and the mixture is agitated until a paste is formed. 697.2 ml of water having been cooled to 5° C. is added, and agitation is subsequently applied until the thickener/water paste is completed dissolved. 15 gm of Methocel is then added slowly with agitation until the thickener is completely dissolved. 10 gm Tergitol is added, and the resulting mixture is blended and set aside.

Step 2: In a second reaction vessel, 40 gm ceresine, 30 gm stearyl alcohol, 20 gm Methocel, and 10 gm Tergitol are heated to 72° C. while agitation is supplied.

Step 3: The mixture of Step 1 above is heated to 72° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 505 gm of the cream base of A above is mixed with 25 gm of Vitamin E until the two components are well dispersed. Next, 450 gm of sucrose is added and the mixture is agitated thoroughly. 20 gm of finely divided silicon dioxide is then added, whereupon the composition is agitated until the final product is homogenous.

EXAMPLE 14 COSMETIC CREAM

A. Preparation of the cream base

Step 1: In a suitable reaction vessel, 177.1 ml of water is heated to 93° C.. 1.8 gm of Methocel is then added, and the mixture is agitated until a paste is formed. 708.6 ml of water having been cooled to 5° C. is added, and agitation is subsequently applied until the thickener/water paste is completed dissolved. 15 gm of Ethocel is then added slowly with agitation until the thickener is completely dissolved. 10 gm Tergitol is added, and the resulting mixture is blended and set aside.

Step 2: In a second reaction vessel, 30 gm cetyl alcohol, 30 gm stearyl alcohol, 17.5 gm polythylene glycol 400, and 10 gm Polysorbate 80 are heated to 75° C. while agitation is supplied.

Step 3: The mixture of Step 1 above is heated to 75° C. whereupon the product of Step 2 above is added to the newly heated product of Step 1 under conditions of constant agitation. Agitation is continued until a firm and uniform cream is obtained. The resultant cream base is cooled to room temperature.

B. Preparation of a Storage Stable Topical Composition 505 gm of the cream base of A above is mixed with 35 gm of Vitamin E until the two components are well dispersed. Next, 450 gm of fructose is added and the mixture is agitated thoroughly. 10 gm of finely divided silicon dioxide is then added, whereupon the composition is agitated until the final product is homogenous.

EXAMPLE 15 CREAM BASE SUITABLE FOR DIS-CONTINUOUS PROCESSING

A. Preparation of the cream base

Step 1: In a suitable reaction vessel, 174.35 ml of water is heated to 95° C.. 2.5 gm Methocel is then added, and the mixture is agitated until a paste is formed. 697.40 ml of water having been cooled to 5° C. is added, and agitation is subsequently applied until the thickener/water paste is completely dissolved. 15 gm of Laponite is then added slowly with agitation until the thickener is completely dissolved. 10 gm Tergitol is added, and the resulting mixture is blended and set aside.

Step 2: In a second reaction vessel, 40 gm cetyl alcohol, 30 gm stearyl alcohol, 20 gm polyethylene glycol 400 and 10 gm Polysorbate 80 are heated to 75° C. while agitation is supplied.

Step 3: The mixture of Step 1 above is heated to 75° C. whereupon the product of Step 2 above is added to the newly heated product of Step 1 under conditions of constant agitation. Agitation is continued until a firm and uniform cream is obtained. The resultant cream base is cooled to room temperature.

Step 4: Add 0.75 gm of povidone iodine and agitate until the resulting, preserved cream base is homogenous throughout.

It is clear that the above examples are by way of illustration only and various modifications may be made in the nature of the composition without departing from the spirit and scope of the invention.

What is claimed is:

1. A storage stable topical composition comprising:
   (a) about 5 to about 30% by weight of a cream base wherein said cream base comprises:
      (i) about 5 to about 10% by weight of one or more topically acceptable waxes;
      (ii) about 0.01 to about 5% by weight of one or more topically aceptable thickeners;
      (iii) about 0.5 to about 3% by weight of one or more topically acceptable surfactants; and
      (iv) the balance being substantially water;
   (b) about 0.1 to about 7% by weight of topically active ingredients;
   (c) about 50 to about 95% by weight of a sugar selected from the group consisting of monosaccharides and disaccharides; and
   (d) about 0.5 to about 2.5% by weight of a moisture control agent, wherein the storage stability is increased significantly in comparison to such compositions not having the moisture control agent.

2. A storage stable composition of claim 1 wherein the active ingredient is selected from povidone iodine, bacteriostatic agents, antibiotics, anti-flammatory agents, microbicidal agents and vitamins.

3. A storage stable topical composition of claim 1 wherein the wax is selected from cetyl alcohol, stearyl alcohol, beeswax, natural candelillia, synthetic candelillia, carnauba, jojoba oil and ceresine or a combination thereof.

4. A storage stable topical composition of claim 1 wherein the thickener is a synthetic clay, a cellulose ether, polythylene glycol or a combination thereof.

5. A storage stable topical composition of claim 1 wherein the surfactant is a polyethylene glycol ether or a sorbitan monosleate or a combination thereof.

6. A storage stable topical composition of claim 1 wherein the moisture control agent is finely divided silicon dioxide, anhydrous lanolin or cholesterol.

7. A storage stable topical composition of claim 2 wherein the active ingredient is providone iodine.

8. A storage stable composition comprising:
   (a) about 5 to about 30% by weight of a cream base wherein said cream base comprises:
      (i) about 5 to about 10% by weight of one or more topically acceptable waxes;
      (ii) about 0.01 to about 5% by weight of one or more topically acceptable thickeners;
      (iii) about 0.5 to about 3% by weight of one or more topically acceptable surfactants; and
      (iv) the balance being substantially water;
   (b) about 50 to about 95% by weight of a sugar selected from the group consisting of monosaccharides and disaccharides; and
   (c) about 0.5 to about 2.5% by weight of a moisture control agent, wherein the storage stability is increased significantly in comparison to such compositions not having the moisture control agent.

9. A storage stable cosmetic composition comprising:
   (a) about 5 to about 70% by weight of a cream base wherein said cream base comprises:
      (i) about 5 to about 10% by weight of one or more topically acceptable waxes;
      (ii) about 0.01 to about 5% by weight of one or more topically acceptable thickeners;
      (iii) about 0.5 to about 3% by weight of one or more topically acceptable surfactants; and
      (iv) the balance being substantially water;
   (b) about 0.1 to about 7% by weight of a topically active ingredient;
   (c) about 20 to about 95% by weight of a sugar selected from the group consisting of monosaccharides and disaccharides; and
   (d) about 0.5 to about 2.5% by weight of a moisture control agent, wherein the storage stability is increased significantly in comparison to such compositions not having the moisture control agent.

10. A storage stable cosmetic composition of claim 9, wherein the active ingredient is selected from aloe and vitamins.

11. A storage stable cosmetic composition of claim 9 wherein the wax is selected from cetyl alcohol, stearyl alcohol, beeswax, natural candelilla, synthetic candelilla, carnauba, jojoba oil and ceresine or a combination thereof.

12. A storage stable cosmetic composition of claim 9, wherein the surfactant is polyethylene glycol, sorbitan monooleate or a combination thereof.

13. A storage stable cosmetic composition of claim 9, wherein the thickener is a synthetic clay, a cellulose ether, polyethylene glycol or a combination thereof.

14. A storage stable cosmetic composition of claim 9, wherein the moisture control agent is finely divided silicon dioxide, anhydrous lanolin or cholesterol.

* * * * *